United States Patent [19]

Eley et al.

[11] Patent Number: 5,320,906
[45] Date of Patent: Jun. 14, 1994

[54] DELIVERY VEHICLES WITH AMPHIPHILE-ASSOCIATED ACTIVE INGREDIENT

[75] Inventors: Crispin G. S. Eley, Fullerton; Paul G. Schmidt, San Marino; Gary Fujii, Brea, all of Calif.

[73] Assignee: Vestar, Inc., San Dimas, Calif.

[21] Appl. No.: 842,271

[22] Filed: Dec. 20, 1991

Related U.S. Application Data

[63] Continuation of Ser. No. 777,468, Oct. 16, 1991, abandoned, which is a continuation of Ser. No. 342,726, Apr. 24, 1989, abandoned, which is a continuation of Ser. No. 942,093, Dec. 15, 1986, abandoned.

[51] Int. Cl.$^5$ .............................................. A61K 9/133
[52] U.S. Cl. ............................ 428/402.2; 264/4.1; 424/428; 424/450; 436/173; 436/829
[58] Field of Search .................. 264/4.1, 4.3; 428/402.2; 424/428, 450, 463, 502; 436/829

[56] References Cited

U.S. PATENT DOCUMENTS

| 7,338 | 1/1987 | Forssen . | |
|---|---|---|---|
| 3,764,540 | 10/1973 | Khalafalla | 252/62.55 |
| 3,848,540 | 10/1974 | Reimers | 252/62.52 |
| 3,917,538 | 11/1975 | Rosenweig | 252/62.51 |
| 4,019,994 | 4/1977 | Kelley | 252/62.52 |
| 4,192,859 | 3/1980 | Mackaness et al. | 424/4 X |
| 4,208,294 | 6/1980 | Khalafalla et al. | 252/62.52 |
| 4,331,654 | 5/1982 | Morris | 424/450 |
| 4,448,765 | 5/1984 | Ash et al. | 424/450 |
| 4,534,899 | 8/1985 | Sears | 260/403 |
| 4,551,288 | 11/1985 | Kelly | 264/4.6 |
| 4,565,696 | 1/1986 | Heath et al. | 424/88 |
| 4,652,257 | 3/1987 | Chang | 604/52 |
| 4,675,173 | 6/1987 | Widder | 424/9 |
| 4,728,575 | 3/1988 | Gamble et al. | 428/402.2 |
| 4,849,210 | 7/1989 | Widder | 424/9 |

FOREIGN PATENT DOCUMENTS

| 45307 | 3/1984 | Australia . | |
|---|---|---|---|
| 50225 | 4/1989 | Australia . | |
| 1252950 | 4/1989 | Canada . | |
| 0094692 | 11/1983 | . | |
| 0198765 | 4/1986 | European Pat. Off. . | |
| 0187702 | 7/1986 | European Pat. Off. . | |
| 0317120 | 5/1989 | European Pat. Off. . | |
| WO87/02364 | 4/1987 | PCT Int'l Appl. . | |
| 2135647 | 9/1984 | United Kingdom | 424/450 |

OTHER PUBLICATIONS

Chang, Chemical Abstracts Selects: Controlled Release Technology, Issue, 10, p. 4, No. 104:155968m (1986).
Charles & Popplewell, IEEE Trans. Magn., vol. MAG-16, No. 2, p. 172 (1980).
Khalafalla & Reimers, IEEE Trans. Magn., vol. MAG-16, No. 2, p. 178 (1980).
Mann, et al., J.C.S. Comm. 1979, p. 1067 (1979).
Mendonca-Dias, et al., Mag. Res. Med., vol. 3, p. 328 (1986).
Mendonca-Dias, et al., Proc. Soc. Mag. Res. Med., p. 887 (Aug. 1985).
Newbower, IEEE Trans. Magn., vol. MAG-9, No. 3, p. 447 (1973).
Olsson, et al., Proc. Soc. Mag. Res. Med., p. 889 (Aug. 1985).
Olsson, et al., Mag. Res. Imag., vol. 4, No. 2, p. 142 (1986).
Renshaw, et al., Mag. Res. Med., vol. 3, p. 217 (1986).
Saini, et al., Mag. Res. Imag., vol. 4, No. 2, p. 144 (1986).
Sambucetti, IEEE Trans. Magn., vol. MAG-16, No. 2, p. 364 (1980).

Primary Examiner—Richard D. Lovering
Attorney, Agent, or Firm—Lyon & Lyon

[57] ABSTRACT

Delivery vehicles comprising an outer biocompatible encapsulating layer, an inner amphiphilic active ingredient-associated layer and an active ingredient are described. The delivery vehicles are biocompatible and are capable of solubilizing the active ingredient for in vivo delivery to bodily tissue or other bodily systems. Uses include nuclear magnetic resonance imaging and therapeutic drug delivery.

21 Claims, 6 Drawing Sheets

PHOSPHOLIPID    CHOLESTEROL

PHOSPHOLIPID    CHOLESTEROL    AMPHIPHILE    ACTIVE INGREDIENT

PHOSPHOLIPID   CHOLESTEROL   AMPHIPHILE   ACTIVE INGREDIENT

PHOSPHOLIPID   CHOLESTEROL   AMPHIPHILE   ACTIVE INGREDIENT

DELIVERY VEHICLES WITH AMPHIPHILE-ASSOCIATED ACTIVE INGREDIENT

This is a continuation of co-pending application Ser. No. 07/777,468 (filed on Oct. 16, 1991 and now abandoned), which is a continuation of Ser. No. 07/342,726 (filed Apr. 24, 1989 and now abandoned), which is a continuation of Ser. No. 06/942,093 (filed Dec. 15, 1986 and now abandoned).

FIELD OF INVENTION

This invention relates to active ingredient delivery vehicle compositions which incorporate an outer biocompatible encapsulating layer, an inner amphiphilic active ingredient-associated layer and an encapsulated material constituting an active ingredient. Also provided are methods for the production of such compositions. These compositions are suitable for solubilizing aqueous-insoluble or aqueous-soluble active ingredients into solvents of interest, and in particular for solubilizing active ingredients for in vivo delivery to bodily tissue or other bodily systems. Specific targeting or delivery of this composition to particular tissues, organs or cells is achieved, as well as extended circulation and serum stability. Active ingredients suitable for use herein include superparamagnetic and ferromagnetic materials such as magnetite for, e.g., nuclear magnetic resonance imaging, halogenated compounds for, e.g., x-ray contrast imaging, radioisotopic compounds for radiographic purposes, other diagnostic agents, and therapeutic agents, including proteins, enzymes, antineoplastics, antifungals, etc.

BACKGROUND

Phospholipid micellar particles in the form of unilamellar or multilamellar vesicles, also known as liposomes, have been used in a number of contexts as vehicles for the solubilization and delivery of active ingredient materials. Liposomes have proven in some cases to be highly advantageous in in vivo delivery systems in terms of biological compatibility, ability to isolate and solubilize otherwise insoluble and/or toxic active ingredients and ability selectively to deliver active ingredients to specific tissues or systems of interest.

Efforts have been made to solubilize ferromagnetic materials in liquid carriers in order to achieve ferromagnetic fluids since at least the early 1960's. One such example is that of magnetite, a ferromagnetic material of formula $Fe_3O_4$ often formed by precipitation from alkaline solution of iron (II) and iron (III) chlorides. Examples of such precipitation methods include those described in Mann et al *J.C.S. Chem. Comm.* 1979, pp. 1067-1068, Khalafalla et al., *IEEE Trans. Magnetics*, Vol. MAG-16, No. 2, pp. 178-183 (March 1980) and Molday et al., *J. Immunological Methods*, Vol. 52, pp. 353-367 (1982). The ability of magnetite to act as a $T_2$ relaxation enhancer in nuclear magnetic resonance has been recognized in the literature. See Ohgushi et al , *J Magn. Res.*, Vol 29, pp. 599-601 (1978).

A number of successful techniques for solubilizing magnetite have been developed, but none prior to the present invention has been demonstrated as being suitable for in vivo use as a delivery vehicle for magnetite having extended circulation time, serum stability and biocompatibility. For example, particulate magnetite, whether uncoated or with coatings known in the prior art, is typically removed from the blood within a very short time, usually in less than one hour and in many cases within five minutes. Moreover, lack of proper solubilization of such particles may lead to aggregation in the body and resultant deleterious effects.

Solubilization of magnetite in non-aqueous solution has been achieved by ball-milling the material in the presence of a surfactant such as oleic acid, by peptization into the desired solvent with a surfactant, and by related methods. In this regard, see Charles et al., *IEEE Trans. Magnetics*, Vol. MAG-16, No. 2, pp. 172-177 (March 1980), Khalafalla et al., U.S. Pat. No. 3,764,540 (1973), and Reimers et al., U.S. Pat. No. 3,843,540 (1974). Characteristic of such non-aqueous, non-polar solvent suspensions of magnetite are vehicles comprising a monolayer coating of surfactant with the polar head thereof associated with the ferrite surface and the lipophilic hydrocarbon tail thereof exposed outwardly to achieve compatibility with the non-polar carrier solvent. Such compositions are not suitable for solubilization in the aqueous environment of the body.

Aqueous or polar solvent suspensions of magnetite have also been achieved. Monolayer surfactant coats of dodecylamine or dodecanoic acid on magnetite have been shown to yield dispersions of the ferromagnetic material, the latter surfactant giving a dilution-stable dispersion. Khalafalla et al., *IEEE Trans. Magnetics*, Vol. MAG-16, No. 2, pp. 178-183 (March 1980). Aqueous ferrofluids using petroleum sulfonates as dispersing agents have been decribed. Kelley, U.S. Pat. No. 4,019,994 (1977). The structure of such monolayer surfactant-coated particles is similar to that of the non-aqueous solubilized magnetite particles discussed above, with prevention of aggregation but retention of water solubility being achieved by virtue of shorter (less hydrophobic) hydrocarbon tails exposed to the solvent phase.

Stable aqueous suspensions of magnetite particles have also been achieved using ionic and non-ionic surfactants to produce a surface double layer. Such structures involve an inner layer of amphiphilic molecules coated on the magnetite particle as in the monolayer case, and an outer surfactant layer oriented with lipophilic tails disposed inwardly and hydrophilic heads exposed outwardly to the aqueous/polar solvent. The inner layer frequently is composed of oleic acid. Materials used as outer surfactants include fatty acids and their salts, long chain ethers or esters, and alkylaromatics such as alkylaryl polyethers. Examples of such bilayer compositions are given in Shimoiizaka, Japanese Patent No. 51-44580 (1976) and Sambucetti, *IEEE Trans. Magnetics*, Vol. MAG-16, No. 2, pp. 364-367 (March 1980). The outer layer surfactants which have thus far been shown to be useful in solubilizing magnetite particles are not, however, suitable for in vivo use inasmuch as they are themselves toxic and are, moreover, rapidly broken down in the blood environment potentially to allow harmful aggregation of the encapsulated materials.

Alternate means of preparing magnetite for in vivo administration include attachment of the particles to micrometer-sized carbohydrate matrices (Olsson et al., *Proc. Soc. Magn. Res. Med.*, p. 889 (4th Ann. Mtg. Aug. 1985) and Olsson et al., *Magn. Res. Imaging*, Vol. 4, No. 2, pp. 142-143 (1986)) and coating of magnetite with the mucopolysaccharide chitosan (Yen et al., U.S. Pat. No. 4,285,819 (1981)). It is believed that such compositions, although possibly stable in serum, would quickly be removed from circulation by the reticuloendothelial system. Magnetically localizable polymerized liposomes containing pharmaceuticals and a ferrite material have been described in Chang, U.S. patent application Ser. No. 714,411 (March 12, 1985) now U.S. Pat. No. 4,652,257. In addition, the encapsulation of magnetite within the enclosed volume of a single bilayer phosphatidylcholine vesicle and a proposal for use in nuclear magnetic resonance spectroscopy is disclosed in Mann et al., *J.C.S. Chem. Comm.* 1979, pp. 1067–1068 (1979). The utility and safety of such a vesicle in this regard is not demonstrated. Furthermore, the composition described would have limited in vivo stability, making it undesirable as an imaging agent. In contrast, the delivery vehicles of the present invention have high stability in serum at 37° C., are capable of extended circulation time, and are biocompatible.

The problems inherent in achieving a solubilized form of magnetite suitable for in vivo use are often applicable to other active ingredients. In particular, such ingredients may be particulate, aqueous-insoluble or toxic in nature, or it may be useful or necessary to deliver them to specific bodily sites. Furthermore, prior art delivery vehicles frequently do not have sufficient serum-stability to achieve optimal results in a safe manner.

Accordingly, the present invention addresses the need to develop improved compositions and methods capable of safely and specifically delivering active ingredients, such as therapeutic agents or diagnostic agents, including magnetic or other imaging agents, to the body in amounts effective to achieve beneficial results.

SUMMARY OF THE INVENTION

The present invention relates to biologically compatible compositions capable of delivering soluble or insoluble active ingredients within living systems. The compositions include an active ingredient and a first layer comprising an amphiphilic material capable of encapsulating or associating with the solid active ingredient through association of the polar head of the amphiphile molecule(s) with the active ingredient. A second outer layer comprises a material, such as, for example, a phospholipid, capable of encapsulating or associating with the amphiphile-coated structure in a manner which renders the delivery vehicle as a whole biocompatible. An appropriate "biocompatible" delivery vehicle will be non-toxic and non-immunogenic to the recipient, both as an intact composition and as breakdown products, if any. Thus, the encapsulating outer layer in the intact composition must present a biocompatible "surface" to the recipient, and is preferably composed of a material which would itself be biocompatible if the delivery vehicle were broken down in the body. In the case of a phospholipid outer layer, the lipophilic tails of the phosphoglyceride associate with the lipophilic tail(s) of the amphiphile, thus stabilizing the amphiphile-active ingredient structure within a phospholipid layer. The exposed polar heads of the phosphoglycerides allow solubilization of the composition in the in vivo environment. Such a composition is biologically compatible by virtue of the phosphoglyceride nature of the exposed surface, and is moreover highly stable in serum and capable of extended circulation in the body.

Active ingredients suitable for use in the compositions of the present invention are characterized in that they are capable of being effectively encapsulated as an aggregate by the amphiphilic layer, or associated on a molecular level with one or more amphiphile molecules. Microcrystalline structures, such as that of magnetite, are suitable active ingredients, as are radionuclides, x-ray contrast imaging agents, and the like. Therapeutic drug agents, such as the antifungal drugs amphotericin B and miconazole and the chemotherapeutic drugs bisanthrene and cisplatin may also be successfully encapsulated or associated with amphiphiles. The active ingredient phase may range in size from individual molecules to aggregates or particles 60 nm or more in diameter. In the case of individual molecules of active ingredient, each molecule may be associated with as few as one amphiphilic molecule.

The amphiphile material will be characterized in that it will be capable of being encapsulated by the outer biocompatible material layer. The particular amphiphile type most useful in a given formulation will depend on the nature of the active ingredient and the surrounding biocompatible material. Saturated or unsaturated fatty acids having from 10 to 28 carbons in the hydrophobic chain are particularly useful, with myristic acid (fourteen carbon chain length) being especially preferred in the case of the active ingredient magnetite. Dialkoylphosphatidic acids are also useful amphiphiles. Both palmitic acid and distearoyl phosphatidic acid have been shown to be effective amphiphiles in the case of the active ingredient amphoteracin B.

Where a phospholipid-encapsulated delivery vehicle is used, targeting of specific organs, tissues, cells or other systems in the body may be achieved in a manner similar to that seen with liposomes previously known in the art. Thus, specific cells such as tumor cells, or specific organs such as the liver or spleen, may be selectively targeted for delivery of spectrometric, radiometric, medicinal or other agents. Moreover, due to the effective isolation of the active ingredient which may be achieved by virtue of the encapsulating amphiphilic and phospholipid layers, any toxicity of the active ingredient may be reduced and/or targeted to specific sites in the body. The delivery vehicle exhibits extended circulation time and stability in serum at 37° C.

Accordingly, the present invention in one aspect provides novel and useful compositions capable of safely delivering active ingredients to the human or other mammalian bodies in amounts effective to achieve beneficial results. It should be recognized, however, that in vivo administration is not the only mode contemplated, and that the advantages inherent in the present invention, including enhanced solubilization of active ingredients, may be utilized in in vitro or other non-living systems or applications.

In another aspect, the present invention provides compositions for delivering magnetic, radiometric, x-ray contrast or other biological imaging agents to the body. In particular, the compositions are useful in delivering ferromagnetic agents such as magnetite for the purpose of nuclear magnetic resonance imaging.

In another aspect, the compositions provide means for delivering therapeutic agents in a safe manner and in effective quantities.

The present invention also provides methods for making the compositions disclosed herein.

DETAILED DESCRIPTION

The present invention provides compositions for the encapsulation and improved delivery in in vivo systems of aqueous-soluble or aqueous-insoluble active ingredients. The compositions exhibit the advantages associated with liposomal delivery vehicles or vesicles by virtue of their phospholipid outer coating, although the compositions need not be liposomal per se in structure, nor consist of phospholipid. The delivery vehicles are capable of incorporating and delivering active ingredients of poor solubility, or which cause irritation when administered by conventional means, or which are to be delivered by an altered biodistribution scheme.

Active ingredients susceptible to encapsulation within the vesicular delivery vehicles of the present invention include a broad range of therapeutic and diagnostic agents. Appropriate therapeutic agents include analgesics, antibacterials, antibiotics, antifungal agents, anti-inflammatory agents, antineoplastics, antiparasitics, antiviral agents, cardiovascular preparations, cell receptor binding molecules, neurotransmitters, ophthalmologicals, polysaccharides and proteins including enzymes, hormones, glycoproteins, immunomodulators, etc. Appropriate diagnostics-related active ingredients include those useful for angiography, CT scan imaging, nuclear magnetic resonance imaging, radiography, X-ray contrast imaging, ultrasound, etc. Particular diagnostic active ingredients include superparamagnetic and ferromagnetic materials such as magnetite, halogenated compounds, radioisotopic compounds, fluorescent compounds and dyes.

Figure 1:
FIG. 1 is an enlarged diagrammatic representation of a typical liposomal delivery vehicle.

Referring to FIG. 1, a typical unilamellar liposome vesicle has a phospholipid bilayer with an enclosed inner volume surrounded by the bilayer. Active ingredients may be incorporated into and encapsulated within this inner volume, surrounded by what will be referred to herein as an "encapsulating layer," which in this case is a phospholipid bilayer. A polar solution in this region is compatible with the stable liposome structure because of attractive interactions between the inner polar solvent and the inwardly-oriented polar portions of the phospholipid molecules of the inner liposomal layer. Alternately, lipophilic active ingredients may be incorporated into and encapsulated within the hydrophobic intra-bilayer region of the liposome (that is, within the encapsulating layer).

Figure 2:
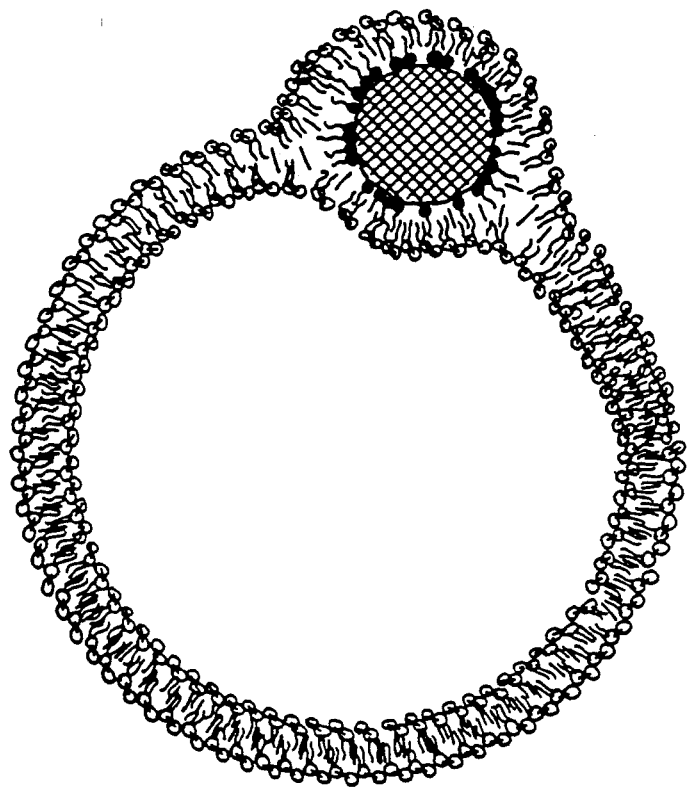
FIG. 2 is an enlarged diagramatic representation of a delivery vehicle of the present invention, wherein an active ingredient phase is associated with amphiphilic molecules and incorporated into the intra-bilayer region of an encapsulating material.

FIG. 2 depicts one form of the compositions of the present invention. In this form, an active ingredient is associated with an encapsulating outer layer through incorporation into and encapsulation within the hydrophobic region within the membranal phospholipid bilayer of a liposome. In order to achieve a stable structure of this type, including an association between the active ingredient phase and the encapsulating layer of the delivery vehicle, it is essential that the active ingredient be compatible with this hydrophobic intra-bilayer region of the encapsulating layer. The present invention achieves such compatibility by virtue of a layer, or other active ingredient-associated group, of amphiphilic molecules applied to the active ingredient in a manner which exposes the lipophilic portions of the amphiphilic molecules outwardly to interact with the hydrophobic intra-bilayer region. Such a structure comprising an active ingredient particle and its associated amphiphilic molecules will be referred to herein as an "Amphiphile-Associated Substrate," or "AAS". The active ingredient in such a magnetite AAS is associated with and stabilized within the intra-bilayer region by virtue of the intermolecular compatibility and attractive forces between the lipophilic portions of the phospholipid or other encapsulating molecules and the amphiphilic molecules. This layer may constitute the outer encapsulating layer of the delivery vehicle, in which case it will comprise a material which renders the delivery vehicle as a whole biocompatible. Alternately, additional encapsulating layers may exist, as in multilamellar vesicles, which may themselves be associated with amphiphile-associated substrates. The outer encapsulating layer of the delivery vehicle will comprise a material which renders the delivery vehicle as a whole biocompatible, i.e., having an acceptable level of non-toxicity and non-immunogenicity to the recipient. (Of course, the active ingredient may be selected so as to exhibit controlled toxicity, as, for example, to targeted cancer cells.) Thus, the outer biocompatible encapsulating layer must present a non-toxic and non-immunogenic "surface" to the recipient. Futhermore, if the delivery vehicle is broken down within the body, the components thereof should be non-toxic and non-immunogenic. It is therefore preferred that the encapsulating layer or layers themselves be composed of a material which is biocompatible upon breakdown in the body, if such occurs.

It is believed that the size of the active ingredient phase or AAS as shown in FIG. 2 may vary significantly while still preserving a stable and effective delivery vehicle. Thus, in the case of the active ingredient magnetite, it has been shown that the diameter of the microcrystalline magnetite particle or particles within the bilayer may be as much as two or more times greater than the thickness of a phospholipid bilayer not associated with any incorporated solid active ingredient, as for example in the liposome of FIG. 1. For example, a liposome of a size useful for delivery of active ingredients to bodily tissues or organs may have an overall diameter of approximately 35 nm to 100 nm, preferably 50 nm to 80 nm, and a "nominal" phospholipid bilayer thickness of approximately 4 to 7 nm (as measured between opposing polar head groups in the membrane without any active ingredient enclosed therein). It has been found that a magnetite microcrystal having a mean diameter of approximately five to 20 nm, and most probably around 11 nm, may be associated with appropriate amphiphilic molecules to form an AAS having a diameter of about 15 nm and then encapsulated within the bilayer of a phospholipid vesicle with a nominal bilayer thickness of only about 5 nm and an overall liposomal diameter of about 60 nm. It is probable that the bilayer structure in such a case must be capable of significant distortion in order to accomodate active ingredients of such relatively large size. Nevertheless, it has been shown in freeze fracture and negative stain electron microscopy investigations relating to the present invention that such structures are possible. Their effectiveness as delivery vehicles has also been demonstrated.

Magnetite may be produced under a range of conditions by alkaline precipitation from ferrous and ferric chloride solutions. For example, immediately following precipitation, the magnetite may be heated; the precipitate may also be allowed to settle in the presence or absence of a magnetic field. Depending on the method of magnetite preparation, maximizing final incorporation into delivery vehicles may require differing conditions. The maximum incorporation achievable may also be dependent on the magnetite preparation method.

It is often useful to maximize the amount of active ingredient associated with a particular delivery vehicle in order to achieve appropriate levels of activity, including magnetic, radiographic or other imaging activity as well as drug therapeutic activity. Overall size of the delivery vehicle must also be taken into consideration, especially where targeting of delivery to particular regions or cells in the body is sought. It is believed that liposomal and other phospholipid-related delivery agents described herein may vary significantly in size while still yielding effective activity results. Delivery vehicles having a diameter of approximately 50 nm to 80 nm have proven to be particularly useful in the case of targeting specific cells such as tumor cells. Moreover, nuclear magnetic resonance imaging techniques using such delivery vehicles have proven useful where the active ingredient is particulate magnetite of approximately 11 nm or more in diameter as discussed above.

It is important to recognize in this regard that the present invention can be practiced utilizing an intact liposomal vesicle with an effective amount of an active ingredient incorporated into the hydrophobic intra-bilayer region of the liposomal membrane. Because the enclosed inner volume of the vesicle is intact in such a structure, the vesicle may enclose a second active ingredient, as for example an aqueous-soluble medicinal agent in solution form, in addition to the first lipid-bound active ingredient. Such a structure may be useful, for example, in magnetically targeting a therapeutic or other agent to particular bodily regions, or in any application where it is appropriate to deliver simultaneously two or more active ingredients susceptible to encapsulation as described herein.

In certain cases, where the active ingredient phase is relatively large in comparison to the nominal phospholipid bilayer thickness, it is thought that a single particulate aggregate of active ingredient may associate with a single delivery vehicle. FIG. 2 illustrates a delivery vehicle of this type. Nevertheless, it is fully contemplated that more than one aggregate of active ingredient may be coated-with an amphiphilic material and incorporated into the intra-bilayer region while still preserving an intact liposomal structure. As the size of the individual active ingredient aggregate decreases, it becomes possible to incorporate more individual aggregates into the bilayer. Furthermore, where the active ingredient is very finely divided, or where it exists in the form of single unaggregated molecules, accordingly less amphiphilic material will be required to associate with individual particles or molecules of active ingredient in order to achieve stabilization of each active ingredient unit or AAS in the hydrophobic intra-bilayer region.

Figure 3:
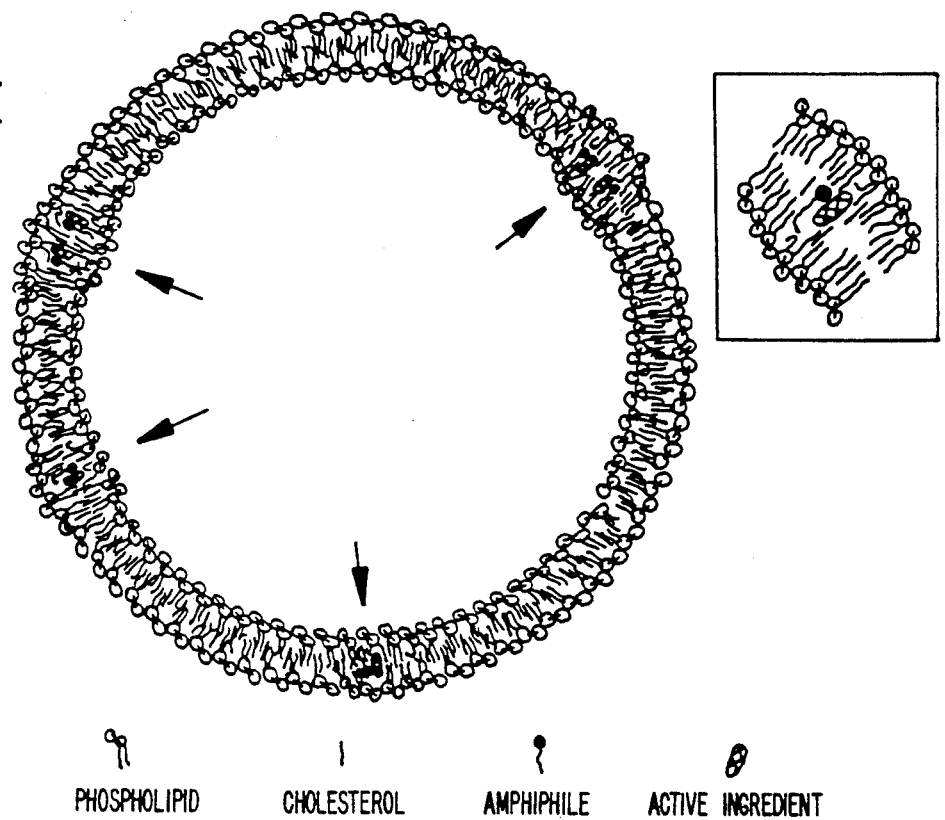
FIG. 3 is an enlarged diagrammatic representation of a delivery vehicle of the present invention, wherein single-molecular or small particulate phases of active ingredient are associated with single molecules of amphiphilic material and incorporated into the intra-bilayer region of an encapsulating material.

In the case of individual molecules of active ingredient, in fact, a monoassociation between a single amphiphilic molecule and a single active ingredient molecule may suffice to stabilize the active ingredient within the bilayer. In such a case a large number of amphiphile-associated substrate particles may be incorporated into the bilayer. FIG. 3 depicts a structure of this type. It is thought that the delivery vehicles of the present invention incorporating the therapeutic antifungal agent amphotericin B may be formulated according to such a structure.

It, however, that active ingredients including amphotericin B may be constituted in solution or otherwise in a variety of forms ranging from individual molecules to particulate aggregates, and each such form would be susceptible to association or coating with an amphiphilic material and incorporation into a delivery vehicle as described herein. Thus, the particular structures described herein are given only by way of example to describe more fully the breadth of the present invention, and are not intended to limit the scope of the invention as claimed.

The structures discussed above and illustrated in FIGS. 2 and 3 are analogous to small unilamellar vesicles (SUVs). Structures containing concentric encapsulating layers may also be utilized within the scope of the present invention. Such structures are analogous to multilamellar vesicles (MLVs). The concentric encapsulating bilayers in such a case may each incorporate amphiphile-associated substrates as described above. The outer encapsulating layer for such a delivery vehicle will generally comprise a material which is itself biocompatible upon breakdown of the delivery vehicle in the body, if such occurs. Accordingly, additional interior encapsulating layers in the MLV-like structure will generally comprise a biocompatible material such as a phospholipid. Such structures would exhibit the properties associated with known MLVs, namely, delayed release of active ingredient, increased amount of encapsulated active ingredient, biocompatibility, etc. Typical sizes for such MLV-like structures would be in the range of from approximately 100 nm to approximately 10,000 nm or more in diameter.

Figure 4:
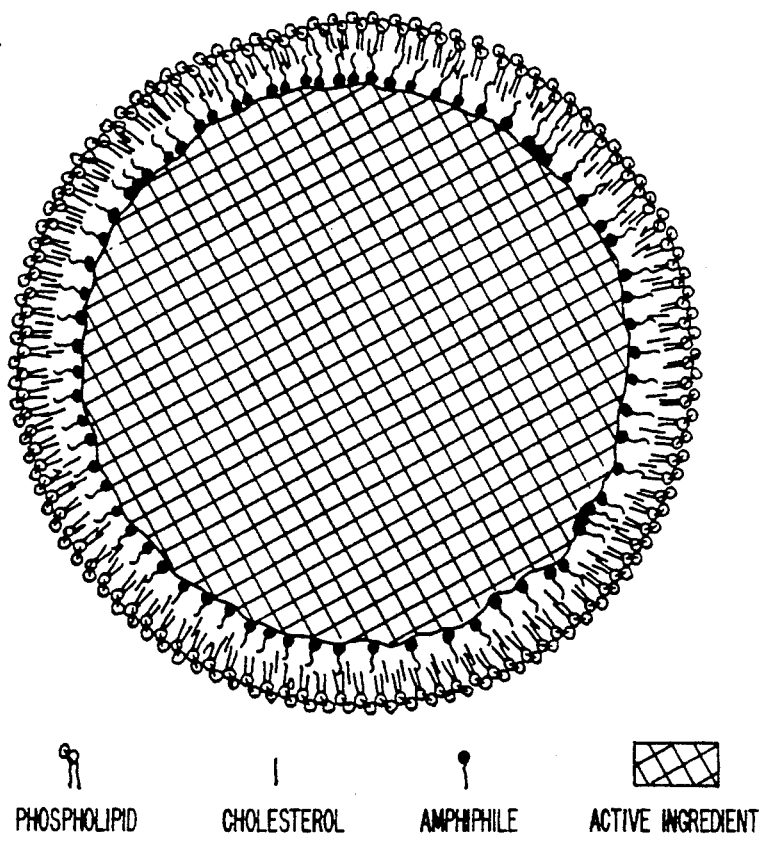
FIG. 4 is an enlarged diagrammatic representation of a delivery vehicle of the present invention, wherein an active ingredient phase is associated with amphiphilic molecules and encapsulated within a monolayer of an encapsulating material.

The present invention also contemplates that the active ingredient may be incorporated into a phospholipid-coated structure as exemplified in FIG. 4. In this case, the amphiphile-coated active ingredient or AAS is not enclosed within the hydrophobic intra-bilayer region of a liposomal structure, but rather is surrounded with an encapsulating layer (in this case, a monolayer) of phospholipid molecules oriented such that the hydrophobic tails of the phospholipid molecules are oriented inwardly and associated with the hydrophobic portions of the amphiphile molecules. The polar hydrophilic heads of the phospholipid molecules are oriented outwardly so as to allow solubilization of the delivery vehicle in aqueous media. The phospholipid nature of the outer coating additionally provides biocompatibility in in vivo systems, as is true with the structures described in FIGS. 1 through 3.

The structure shown in FIG. 4 may be used to accomodate an active ingredient phase that is too large to be enclosed within the intra-bilayer region of a liposomal structure. It is apparent that a larger active ingredient phase will yield a higher concentration of active ingredient for a given number of delivery vehicles. Alternately, it may be desirable to achieve a delivery vehicle which is not liposomal in structure (i.e., has no enclosed solution-phase inner volume) or which is smaller in overall size than that associated with typical liposomes.

Delivery vehicles of the type shown in FIG. 4 may range in size depending on the size of the active ingredient phase. It is contemplated that delivery vehicles of from about 20 nm to about 100 nm in diameter would be particularly useful. However, larger sizes may also be used, as, for example, when the structure of FIG. 4 is incorporated into an MLV-like structure having additional encapsulating layers.

An example of a structure of FIG. 4 is that of microcrystalline magnetite having, for example, particulate diameters of about 40 nm to 70 nm. Particles of this approximate size are known to be useful in targeting certain tumor cells for nuclear magnetic resonance imaging or other applications. Examples of the use of magnetite in nuclear magnetic resonance imaging of tissue is described, for example, in PCT Patent Application Number PCT/N085/00017 (Jacobsen et al.), Saini et al., *Magn. Res. Imaging* Vol. 4, No. 2, p. 144 (1986), Renshaw et al., *Magn. Res. Med.* Vol. 3, pp. 217–225 (1986) and Dias et al., *Magn. Res. Med.* Vol. 3, pp. 328–330 (1986), the disclosures of which are incorporated herein by reference. Appropriate dosages may be determined easily so as to optimize the imaging response, as discussed for example in Example 6 of this specification, and may be administered using well-known techniques such as i.v. or local injection or oral administration. The magnetite particles may be coated with an inner monolayer of amphiphilic molecules and an outer encapsulating monolayer of phospholipid molecules to yield a highly concentrated aqueous-soluble form of magnetite that is simultaneously biocompatible and capable of being targeted to particular bodily sites.

Coating of the prepared active ingredient with an appropriate amphiphile, or association between individual molecules of active ingredient and amphiphile, may generally be achieved by a variety of high shear methods including sonication and homogenization. In the case of aqueous-insoluble active ingredients such as magnetite, it will normally be possible to achieve an aqueous dispersion or suspension of the material suitable for association with the amphiphile during sonication. The initial dispersion may itself be achieved with the aid of sonication. Phosphate-buffered saline (PBS) is an especially useful aqueous solvent where the delivery vehicles are intended for in vivo or other biologically-related use, and especially where the final coating with phospholipid or other material will be achieved in the same solvent batch as is used for the amphiphile coating. Other buffered aqueous solvents, as well as solutions containing ingredients such as dextrose, may be used to achieve an acceptable dispersion of active ingredient. Non-aqueous solvents, or mixtures of aqueous and non-aqueous solvents, may be used in order to obtain an acceptable active ingredient suspension and also to allow proper coating or association of the active ingredient with the amphiphile. For example, an aqueous-organic mixture such as PBS-chloroform may be employed where spray drying of the amphiphile-active ingredient mixture is to be performed. Similarly, an aqueous-organic mixture may be used where a two phase amphiphile coating process is desired.

The choice of amphiphile to be used in a particular formulation will depend on a variety of considerations. The desired association between the amphiphile molecules and the active ingredient arises due to specific interactive forces between the polar portion of the amphiphilic molecules and the active ingredient, as distinct from simple miscibility or solubility of the active ingredient in the amphiphile. Such forces may, for example, be in the nature of ionic or electrostatic bonding between the amphiphile and the active ingredient, covalent bonding, hydrogen bonding, chemisorptive forces or physisorptive forces. The nature of the association between magnetite and such ionic or non-ionic amphiphiles as fatty acids or fatty acid derivatives has been discussed in the literature In this regard, see Khalafalla et al., *IEEE Trans. Magnetics*, Vol. MAG-16, No. 2, pp. 178–183 (March 1980). In the case of other active ingredients such as amphotericin B, it is thought that ionic charges on functional groups in the active ingredient molecule (such as a positive charge on the amino group in amphotericin B) may interact with negatively-charged head groups on, for example, fatty acids or phosphatidic acid. Covalent linkages between the active ingredient and the amphiphile may also in proper cases be utilized to associate these molecules or particles.

The choice of a proper amphiphile will depend on considerations of achieving an association with the active ingredient and in addition on the nature of the nonpolar or hydrophobic portion of the amphiphile. An amphiphile is considered to be a molecule having both a hydrophilic portion and a hydrophobic (or lipophilic) portion. An amphiphile suitable for use in the present invention will be capable of associating via its hydrophilic group with an active ingredient as discussed above. In addition, the nature of the amphiphile should be such that, upon association with the active ingredient, the resultant amphiphile substrate particle (AAS) is compatible with, and associated with, the encapsulating layer. This association may be in the nature of "solubilization" of the AAS within an amphiphile-associated substrate-encapsulating material, as illustrated for example in FIGS. 2 and 3. Alternatively, this association may result from hydrophobic or lipophilic interactions between the hydrophobic portions of the AAS and the encapsulating material, as illustrated for example in FIG. 4. This associative interaction is distinct from, for example, the use of a phospholipid-immiscible material containing an active ingredient which forms a phase that is immiscible with the encapsulating layer, as described in Sears et al., U.S. Pat. No. 4,298,594.

The hydrophilic portion of the amphiphile may be a charged or uncharged group including, by way of example, carboxylic, hydroxyl, amino, phosphato, or sulfato groups. The hydrophobic portion of the amphiphile may include, by way of example, saturated and unsaturated aliphatic hydrocarbon groups, including polyoxyethylenes, and aliphatic groups substituted by at least one aromatic and/or cycloaliphatic group.

Specifically preferred amphiphiles are the fatty acids, as discussed below. These may be either naturally-occurring or synthetic fatty acids, as well as derivatives thereof. Other appropriate amphiphiles may include phospholipids and compounds related thereto including, for example, phosphatidylcholines (lecithins), phosphatidylethanolamines (cephalins), phosphatidic acids, phosphatidylserines, phosphatidylinositols, phosphatidylglycerols, diphosphatidylglycerols (cardiolipins), plasmalogens, lysophosphoglycerides, and saturated synthetic forms of the foregoing. Other appropriate non-phospholipid amphiphiles may include di- and triglycerides, hydrophobic-substituted-alcohols, -amines, -phosphates and -sulfates, alkyl ether acylglycerols, glycosylacylglycerols, sphingolipids including the sphingomyelins, glycosphingolipids including the cerebrosides, phytols, retinols, and vitamins such as Vitamins A, K, E and D.

Fatty acids and fatty acid derivatives are among the preferred amphiphiles for use in the prevent invention. The hydrocarbon chain may be either saturated or unsaturated. The length of the hydrocarbon chain in a fatty acid or other amphiphile may be optimized to enhance the ability of the outer biocompatible material to encapsulate the amphiphile-active ingredient structure. This in turn may depend on the nature of the hydrophobic portion of, for example, a phospholipid encapsulant. In addition, the overall size of the amphiphile-active ingredient structure will depend on the nature of the amphiphile and will affect the ability to achieve a final delivery vehicle of a desired structure (see FIGS. 2 through 4 and the discussion above relating thereto).

One preferred amphiphile in the present invention is the groups of fatty acids having hydrocarbon chains of from about 10 to about 28 carbons. Particularly preferred are fatty acids with 14 to 24 carbons. Where the outer encapsulating material comprises phospholipids such as distearoylphosphatidylcholine and cholesterol and the active ingredient is magnetite, tetradecanoic acid (14 carbons), palmitic acid (16 carbons), docosanoic acid (22 carbons) and tetracosanoic acid (24 carbons) are especially preferred. In practice, shorter amphiphiles such as tetradecanoic acid and palmitic acid may be preferable from the standpoint of non-toxicity. Palmitic acid is also preferred for the active ingredient amphotericin B. Phosphatidic acids having saturated or unsaturated hydrocarbon chain lengths of from about 10 to about 20 carbons (two chains per molecule), and in particular 16 to 18 carbons, are especially preferred amphiphiles for amphoteracin B. Amphiphiles having positively-charged polar groups would be particularly useful where the active ingredient may be negatively-charged or is electron-donating.

Figure 6:
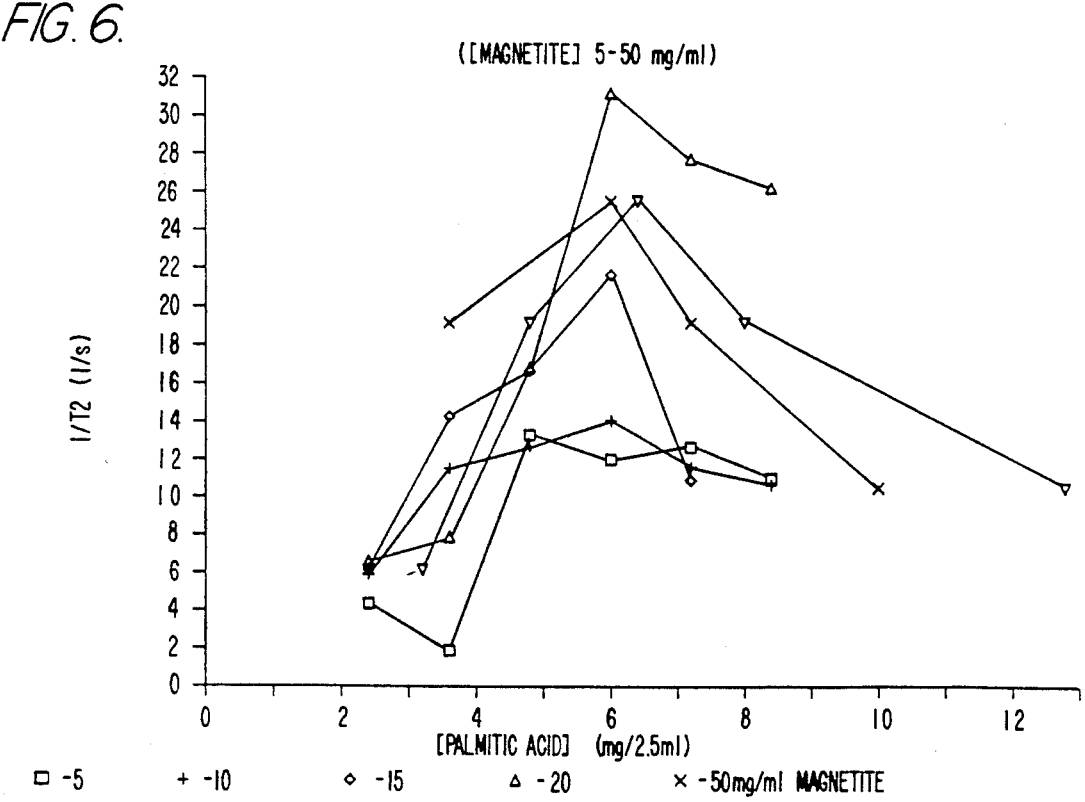
FIG. 6 is a graphical representation showing the correlation between NMR relaxation rate enhancement and incorporated active ingredient (magnetite) concentration.

Association of the amphiphile with the active ingredient may be achieved by known methods including bore milling, homogenization and sonication. In the case of solution phase sonication or other methods where it is desirable to optimize the concentration and amount of amphiphile to be combined with a given amount of active ingredient, an optimum concentration may initially be estimated by comparing the aggregate surface area of the active ingredient to be treated with the steric size of the amphiphile as it occupies a portion of the active ingredient surface. In practice, a range of amphiphile concentrations may be acceptable. Experiments have shown that a maximization of the concentration of active ingredient in the final delivery vehicle preparation may in fact depend on optimizing the initial amphiphile concentration. FIG. 6 shows a broad peak in NMR $T_2$ relaxation rate enhancement associated with magnetite delivery vehicles of the present invention occurring at an initial palmitic acid concentration of around 6 mg of palmitic acid per 2.5 ml of starting magnetite dispersion. Similar optimization may be achieved for other formulations of the present invention.

Sonication of active ingredients, amphiphile, and biocompatible outer layer materials may be performed with, for example, an Ultrasonics, Inc. probe with a microtip at a power of about 50 W to 90 W. Satisfactory sonication generally can be achieved in about 15 minutes. The sonication temperature preferably should be above the melting temperature or phase transition temperature range of the amphiphile.

After sonication of the active ingredient with the amphiphile, an appropriate encapsulating layer or layers may similarly be added with the aid of sonication or other methods known in the art to achieve a biocompatible delivery vehicle. Particularly preferred in the present invention as biocompatible materials are phospholipids and phospholipid-cholesterol mixtures. Appropriate phospholipids may be used singly or in combination, and include both naturally-occurring and synthetically-prepared phosphatidylcholines, phosphatidic acids, phosphatidylserines, phosphatidylethanolamines, phosphatidylglycerols and phosphatidylinositols. Phospholipid materials may be obtained in naturally-occurring form, as derived for example from purified egg yolk, or they may be of synthetic form, as for example with saturated synthetic hydrocarbon side chains. Sterols, sterol esters or other materials including cholesterol, cholestanol, cholestane, tocopherol and the like may also be included in the encapsulating layer to increase the stability of the delivery vehicle or to modulate membranal permeability. Cholesterol is particularly preferred for this purpose.

In particular, mixtures of distearoylphosphatidylcholine (DSPC) and cholesterol (CHOL) are preferred materials for delivery vehicle encapsulation. Mixtures in the ratio 2:1 (DSPC:CHOL) are effective in the present invention. Other preferred phospholipids include dipalmitoylphosphatidylcholine (DPPC), dimyristoylphosphatidylcholine (DMPC) and other phospholipids having about 10 to about 20 carbons in their hydrocarbon chains.

The concentration and amount of phospholipid to be used in a particular formulation may vary significantly while still obtaining a satisfactory final composition. Typical concentrations are given in the examples discussed herein. Sonication may be carried out under the same conditions as employed for the amphiphile. The mixture may then be centrifuged for about ten minutes at about 16,000 G and the supernatant filtered to yield a solution containing a composition of the present invention.

The addition of appropriate outer layers may also be achieved by methods typically used for preparation of MLVs. Thus, multiple biocompatible outer layers may, for example, be added by hydration of a phospholipid film in an aqueous suspension of the amphiphile associated substrate by vortex stirring for about 60 minutes at a temperature above the phopholipid phase transition temperature.

It is anticipated that the surface of the delivery vehicle may be modified to provide an altered in vivo biodistribution profile, in much the same way as liposome surfaces are altered. Such modificiation may, for example, consist of attachment of monoclonal antibodies or of ligands with specific binding properties, or the incorporation of glycolipids. Such modifications are described in Schmidt (Ed.), *Liposomes as Drug Carriers* (*Symposium Tubingen, October* 1984, Georg Thieme Verlag (Stuttgart: 1986 ) , Ostro (Ed. ) , *Liposomes*, Marcel Dekker, Inc. (New York: 1983) and Gregoriadas (Ed.) , *Liposome Technology*, Volume III, CRC Press, Inc. (Boca Raton, Fla: 1984), the disclosures of which are incorporated herein by reference.

The delivery vehicles of the present invention may be administered using techniques well known in the medical art, including injection (i.v., i.p. or i.m., for example), inhalation, oral administration, topical administration, intraocular administration and the like. Appropriate dosages may also be determined using known animal and clinical testing procedures, including biodistribution studies on tissue samples as described herein.

EXAMPLE 1

Preparation of Magnetite Delivery Vehicles 25 ml aliquots of 15 mg/ml magnetite in PBS were sonicated (80 W) with varying amounts of palmitic acid (2.4 mg to 10 mg) at 66° C for 15 minutes. The resulting suspensions were then sonicated under the same conditions, with 46 mg of a $^{14}C$ and $^{3}H$ radiolabelled 2:1 DSPC:CHOL lipid film. The product suspension was centrifuged for 10 minutes at 15600 G and the supernatant was passed through a 220 nm filter. The final solutions ranged in appearance from milky white (2.4 mg palmitic acid)—similar to 2:1 DSPC:CHOL small unilamellar vesicles—to clear golden brown (6 mg acid). The intensity of coloration reached a maximum at 6 mg of palmitic acid, a gradation of color being found increasing to the maximum and decreasing, to white, at higher palmitic acid concentrations. The clarity of the solutions followed a similar trend 100 µl aliquots of the solutions were diluted with 10 ml of a suitable solvent and the lipid concentration was determined using a scintillation counter to quantify the radiolabels. On the basis of the concentrations so determined, a 2 mg/ml lipid dilution of each solution was prepared. An IBM Minispec PC/20 was then employed to measure $T_2$ relaxation times of these dilutions. The results are shown in Table 1.

TABLE 1

| Palmitic Acid (mg) | $T_2$ (msec) | $1/T_2$ (sec$^{-1}$) |
|---|---|---|
| 2.4 | 162 | 6.2 |

TABLE 1-continued

| Palmitic Acid (mg) | $T_2$ (msec) | $1/T_2$ (sec$^{-1}$) |
|---|---|---|
| 3.6 | 70 | 14.3 |
| 4.8 | 60 | 16.7 |
| 6.0 | 46 | 21.7 |
| 7.2 | 92 | 10.9 |
| 10.0 | 173 | 5.8 |

The procedure above was repeated using 5, 10, 15, 20 and 50 mg/ml magnetite in PBS. The $T_2$ relaxation rates as a function of the amount of palmitic acid are plotted in FIG. 6.

Figure 5:
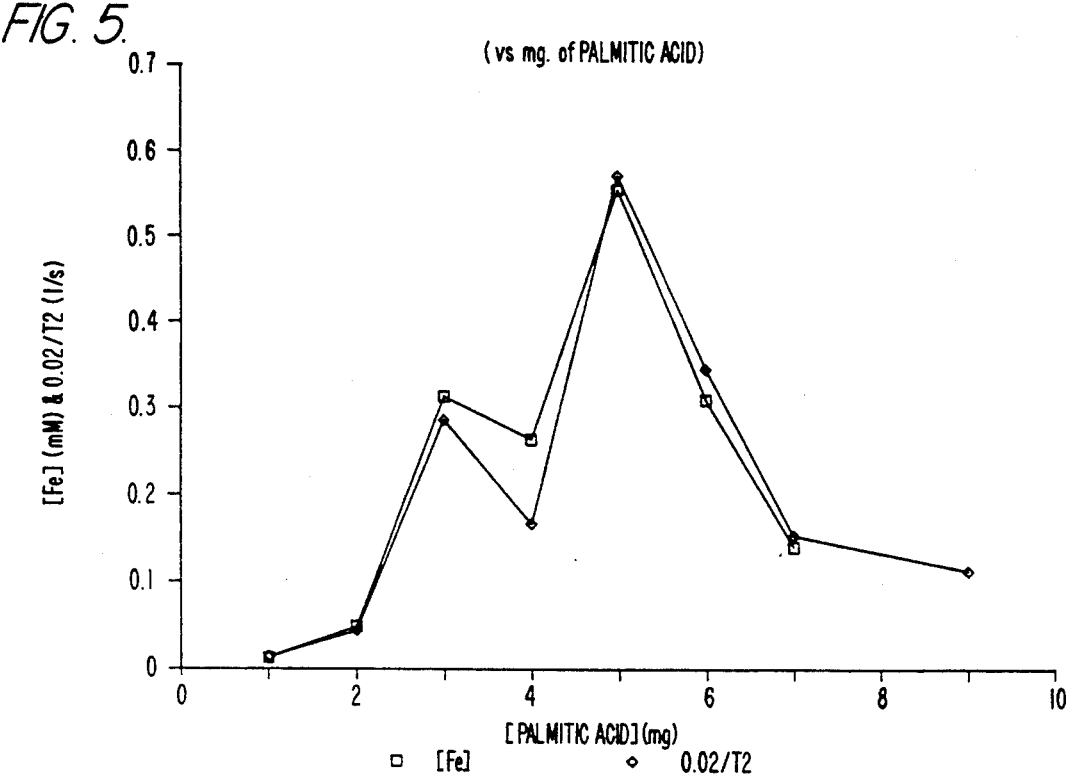
FIG. 5 is a graphical representation showing one correlation between active ingredient (magnetite) incorporation or NMR relaxation rate enhancement and amphiphile formulation concentration.

Samples corresponding to 10 mg/ml magnetite were analyzed for iron as follows: a 100 µl aliquot was heated, with agitation, for 30 minutes at 65° C., with 900 µl HNO$_3$, 100 µl 5M NH$_4$ SCN and 1.4 ml heptanol Following oxidative solubilization of the iron present, bright red Fe(SCN)$_4$—formed in the aqueous phase which was then completely extracted into heptanol, as Fe(SCN)$_3$. Absorbance of the heptanol solution at 498 nm was used to quantitate the Fe(SCN)$_3$ using a molar extinction coefficient determined with FeCl$_3$ standards. Heptanol is necessary for acid catalyzed esterification and extraction of palmitic acid which otherwise remains bound as a protective hydrophobic coating on magnetite particles. FIG. 5 shows the correlation between $T_2$ relaxation rates ($1/T_2$) and iron concentration, with normalization of the latter to constant lipid concentration.

EXAMPLE 2

Preparation of Magnetite Delivery Vehicles—Spray-Drying Method 12 ml of 250 mg/ml magnetite suspension was made up to 30 ml with PBS and then sonicated with 12 wt./wt. % palmitic acid (i.e. 360 mg) in 5 ml chloroform. The resulting suspension was spray dried at 200° C. to yield a magnetite amphiphile-associated substrate (AAS) material as a black powder. 50 mg of this magnetite AAS was sonicated in 5 ml PBS to disperse the powder and the resulting suspension was sonicated with 92 mg 2:1 DSPC:CHOL under previously described conditions. After centrifugation and 220 nm filtration a clear golden brown solution was obtained.

EXAMPLE 3

Preparation of Magnetite Delivery Vehicles—Two-Phase Method

Preparation of the intermediate magnetite AAS was also achieved using a two-phase method. 19.6 mg palmitic acid was dissolved in 2 ml chloroform and this solution was gently sonicated in a cold water bath, for 15 minutes, with 5 ml PBS containing 62.5 mg magnetite. The resulting mixture was centrifuged to yield a lower organic phase covered by a precipitate of magnetite AAS in the upper aqueous phase. The chloroform was removed by pipetting it off and then bubbling dry nitrogen gas through the aqueous phase and the precipitate. Following redispersion of the AAS by sonication, it was further sonicated with 92 mg 2:1 DSPC:CHOL, centrifuged and filtered as in previous examples. The solution obtained after filtration appeared dense black, although when viewed as a thin film it was a clear dark chocolate brown color. Analysis for iron yielded greater than 3.6 mM magnetite (Fe$_{34}$). Dilutions of this solution, in PBS, by factors of 40, 100 and 250 yielded relaxation rates as shown in Table 2.

TABLE 2

| Dilution | $T_2$ (msec) | $1/T_2$ enhancement (sec$^{-1}$) |
|---|---|---|
| 1:250 | 15 | 66 |
| 1:100 | 6 | 166 |
| 1:40 | <4 | >250 |
| control | 1850 | 0 |

Note:
$1/T_2$ (enh) = $1/T_2$ (obs) − $1/T_2$ (control); i.e., rate enhancement = observed rate minus control rate.

EXAMPLE 4

MRI $T_2$ contrast

Magnetite solubilized by the method of Example 1 above was tested for "in vivo" effects on tissue relaxation times. From 5 mg palmitic acid, 2 ml of 5 mg/ml magnetite in PBS and 40 mg 2:1 DSPC:CHOL, a golden brown solution containing 17.5 mg/ml of lipid was obtained. A 2.5:1 dilution of this solution with PBS was also prepared. EMT6 tumor tissue was transplanted subcutaneously into the flank of male Balb/c mice and allowed to grow for 10 days. On the tenth day, mice were injected i.v. with 200 μl of solubilized magnetite solution or control buffer. Mice were sacrificed 24 hours later and tissue samples were excised, rinsed in PBS, blotted, weighed and sealed in plastic bags. NMR relaxation times were then measured for the excised tissues. The results are presented in Table 3 and clearly demonstrate enhanced relaxation rates (observed rate minus control rate), with $T_2$ being more affected than $T_1$.

TABLE 3

| Rate enchancements - biodistribution data | | | |
|---|---|---|---|
| | Liver | Tumor | Spleen |
| $\Delta (T_2^{-1}) (s^{-1})$: | | | |
| 17.5 mg/ml | 4.44 | 4.64* | 9.23 |
| 7.0 mg/ml | 2.16 | 2.40 | 6.78 |
| $\Delta (T_1^{-1}) (s^{-1})$: | | | |
| 17.5 mg/ml | 0.50 | 0.44 | 0.43 |
| 7.0 mg/ml | 0.30 | 0.38 | 0.48 |

EXAMPLE 5

Time Course Of Biodistribution Of Magnetic Delivery Vehicles

Figure 7:
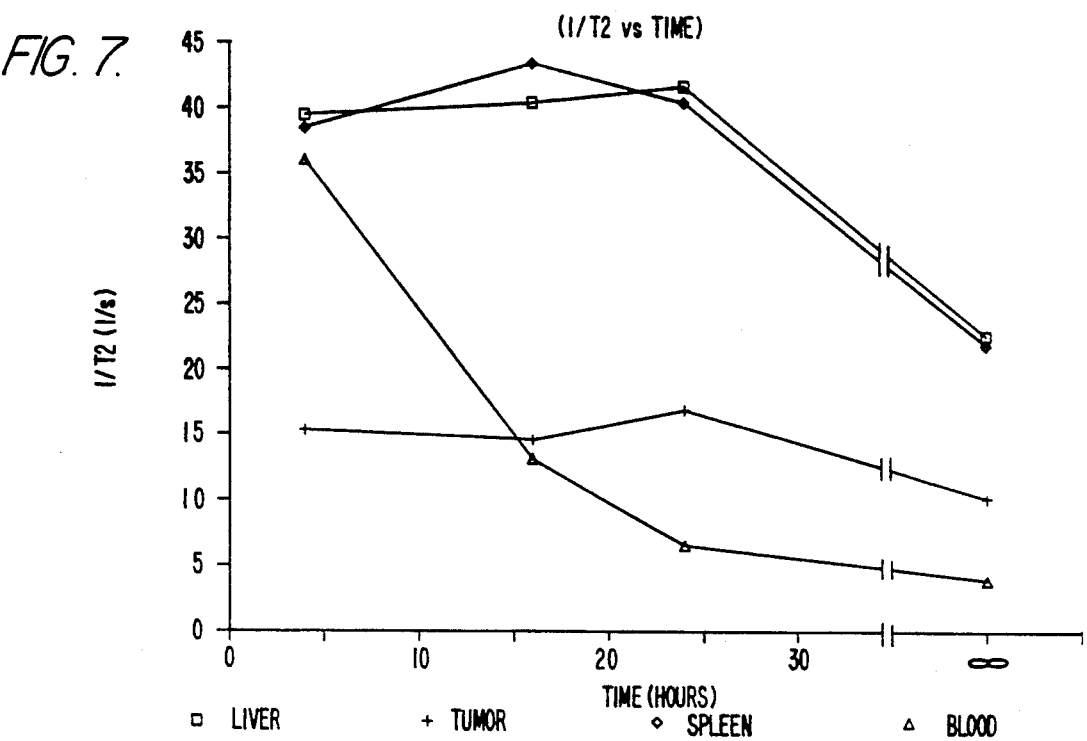
FIG. 7 is a graphical representation showing the time dependence of NMR $T_2$ relaxation rate enhancement in various biodistribution systems.
Figure 8:
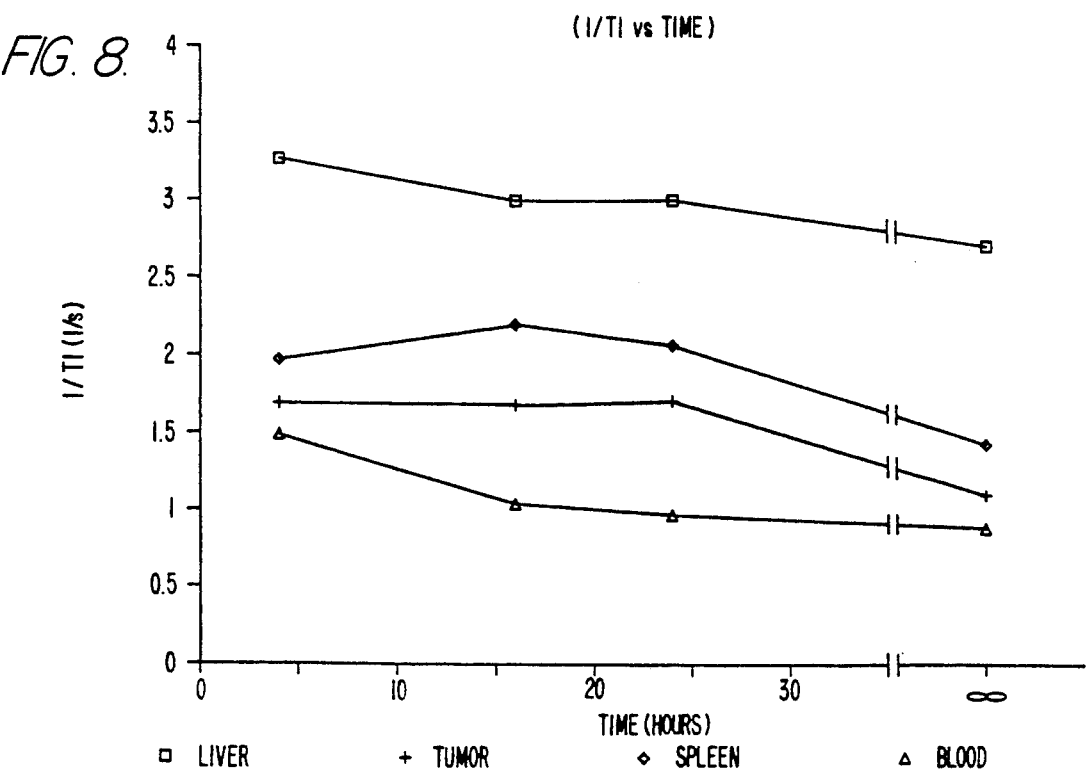
FIG. 8 is a graphical representation showing the time dependence of NMR $T_1$ relaxation rate enhancement in various biodistribution systems.

Solubilized magnetite was prepared according to the method of Example 1 using 5 ml of 8 mg/ml magnetite in PBS, 12 mg palmitic acid and 104 mg 2:1 DSPC:CHOL lipid film. Groups of three tumor-bearing female Balb/c mice were intravenously injected with a control solution, 200 μl PBS (one group) or 200 μl of magnetite solution (three groups). Magnetite-bearing animals were sacrificed at 4, 16 and 24 hours after injection; the control group was sacrificed 27 hours post injection. Tissues were removed immediately and $T_2$ and $T_1$ relaxation times were determined at 38° C. using an IBM Minispec 20. The mean tissue relaxation rates ($1/T_2$ and $1/T_1$) are shown in FIGS. 7 and 8 as a function of time for each tissue, with control values at t=infinity. It is clear that the magnetite delivery vehicles are removed from bloodstream over a period of hours, which contrasts markedly with magnetite particles (with or without coatings) that are typically eliminated from the blood in approximately 5 minutes.

EXAMPLE 6

Dose Dependence Of Tissue Relaxation Times

Figure 9:
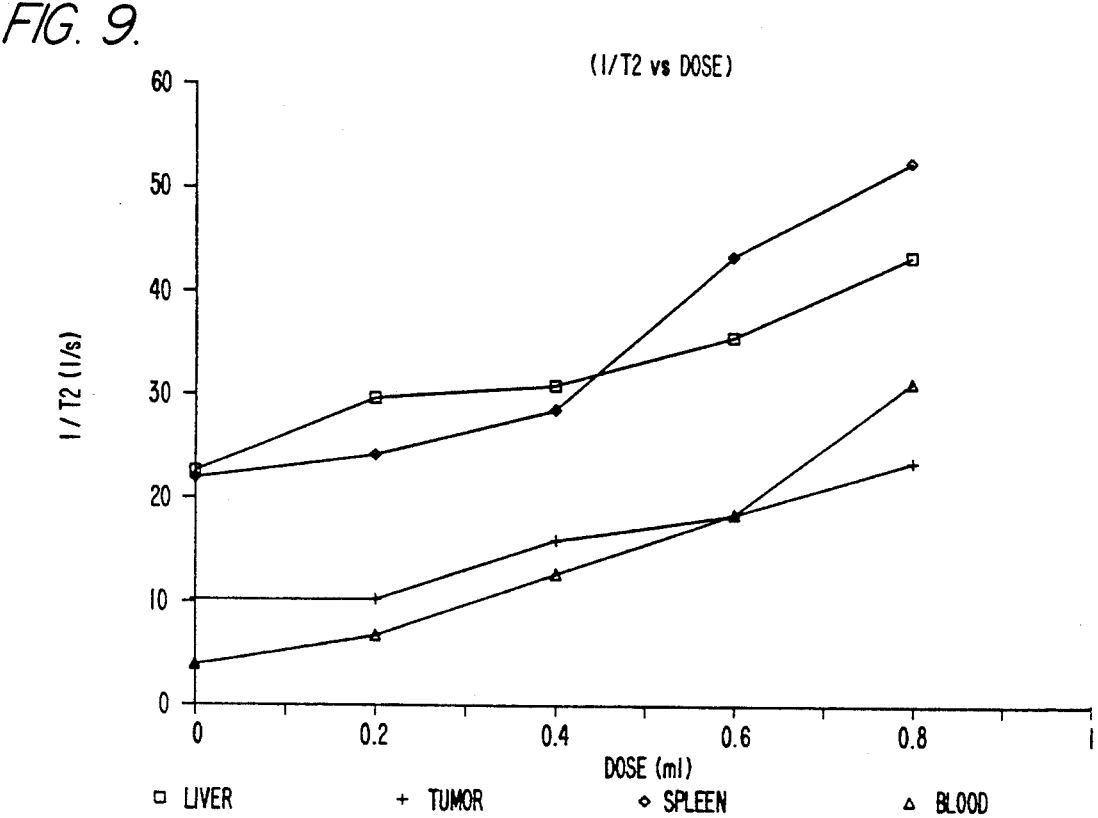
FIG. 9 is a graphical representation showing the dose dependence of NMR $T_2$ relaxation rate enhancement in various biodistribution systems.
Figure 10:
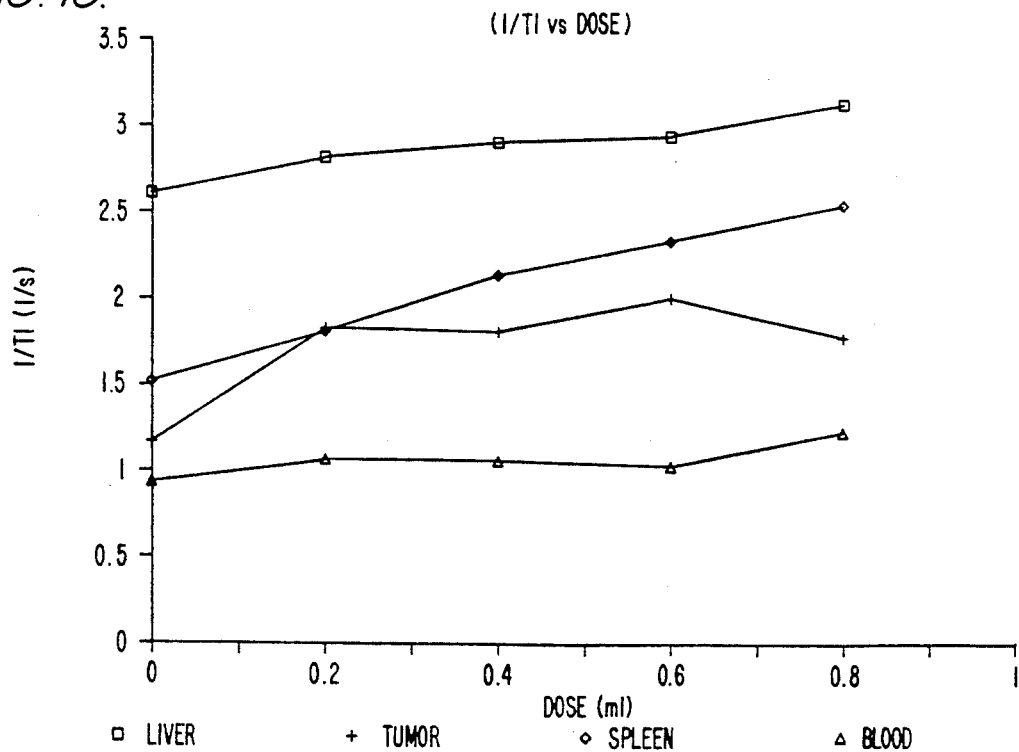
FIG. 10 is a graphical representation showing the dose dependence of NMR $T_1$ relaxation rate enhancement in various biodistribution systems.

Liposomal magnetite was prepared as in Example 1, diluted 50:1 in PBS, 0.80 micron and 0.22 micron filtered and then concentrated by ultra-filtration to yield a final solution containing 8 mg/ml DSPC (as determined by HPLC assay). Varying doses of this solution, and 200 μl of a control PBS solution, were injected i.v. into tumor bearing Balb/c mice. At 24 hours post-injection, tissues were removed and their $T_2$ and $T_1$ relaxation times were determined. The dose dependences of $1/T_2$ and of $1/T_2$ are shown in FIGS. 9 and 10. A significant $1/T_1$ enhancement is only found where intact magnetite particles are present, since dissolution of magnetite removes the cooperative interactions between the magnetic moments of iron atoms. Solubilized magnetite is expected to give a $1/T_1$ increase as compared to the paramagnetic iron species in solution (a small $1/T_2$ increase is also possible). Tumor results in FIGS. 9 and 10 suggest that at low doses all the magnetite arriving at the tumor is solubilized but at higher doses the mechanism for solubilizing the particles is saturated and intact particles cause $T_2$ relaxation enhancement. There is no significant $T_1$ enhancement for liver and blood although $T_2$ enhancement is observed; this is consistent with intact particles. For the spleen, the form of the dose-dependence suggests some dissolution of particles, without saturation of the mechanism for solubilizing them.

EXAMPLE 7

Preferred Range Of Fatty Acid Amphiphiles

Figure 11:
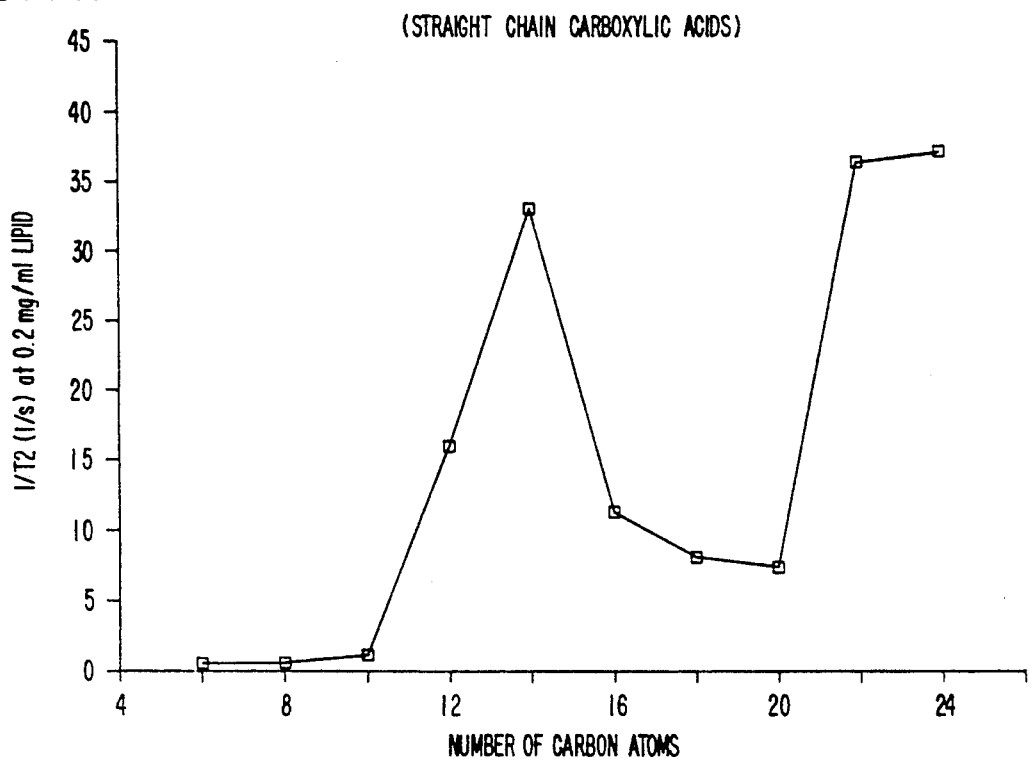
FIG. 11 is a graphical representation showing one correlation between NMR relaxation rate enhancement and amphiphile chain length.

Magnetite-containing delivery vehicles were prepared by the method of Example 1 using equimolar quantities of a range of different fatty acids containing from six to 24 carbon atoms. In each case a magnetite AAS was prepared by sonicating the fatty acid at 65° C. with 5 ml 8 mg/ml magnetite in PBS and subsequently sonicating at 25° C. with 100 mg 2:1 DSPC:CHOL lipid film. A liposome-solubilized magnetite solution was produced in each case, as evidence by solution coloration and by the enhanced $T_2$ relaxation rate found for various dilution in PBS. Representative results are shown in FIG. 11.

EXAMPLE 8

Range of Phospholipid Compositions

Liposome-solubilized magnetite was prepared using the method of Example 1 with 5 ml of approximately 8 mg/ml magnetite in PBS and approximately 12 mg of palmitic acid. Final sonication, at 65° C, was carried out with equimolar amounts of lipid film, the composition ranging from 1:1 DSPC:CHOL to 3:1 DSPC:CHOL. The molar amount of lipid was equivalent to 100 mg 2:1 DSPC:CHOL. The final solution $T_2$ relaxation rates ($R_2'$) at 10:1 dilution in PBS are listed in Table 4.

TABLE 4

| DSPC:CHOL | $R_2$ (sec$^{-1}$) |
|---|---|
| 1:1 | 23.8 |
| 1.5:1 | 23.3 |
| 2.0:1 | 29.4 |
| 2.5:1 | 10.0 |
| 3.0:1 | 6.8 |

EXAMPLE 9

Temperature Dependence

Liposomal magnetite was prepared by the method of Example 1 from 5 ml of 8 mg/ml magnetite solution in PBS and a total of 12 mg docosanoic (behenic) acid. A range of temperatures was employed in the final sonication step, demonstrating that the entrapment efficiency for magnetite is temperature dependent. The relaxation rate of a 10:1 dilution of final solution increased with decreasing temperature of sonication. Thus, for a nominal 85° C. sonication (measured final temperature 74° C.), $R_2$ was found to be 1.4 sec$^{-1}$ increasing to $R_2$ of 27.8 sec$^{-1}$ for 25° C. nominal (45° C. final measured temperature). A further increase of $R_2$ to 31.3 sec$^{-1}$ was noted in final sonication in an iced water bath (below 5° C.), the measured temperature on completion being 41° C. However, in this latter case difficulty of filtration through a 0.22 μm filter of the final product was observed.

EXAMPLE 10

Preparation of Amphotericin B delivery vehicles 5 mg of amphotericin B, an antifungal agent, was sonicated in 5 ml of 10 mM tris-HCl-buffered (pH 7.4) 5 wt./wt. % dextrose solution to generate a dispersion of the insoluble drug. This dispersion was subsequently sonicated with 15 mg palmitic acid and then with 40 mg of 2:1 DSPC:CHOL. The suspension produced was centrifuged at 18000 g for 15 minutes and the supernatant was 220 nm filtered, yielding a clear yellow solution. Spectrochemical analysis for amphoteracin B, by absorbance at 405 nm (E=1.309×10$^5$M cm$^{-1}$), of a 1:100 dilution of the solution in methanol yielded a value of 0.4 mg/ml corresponding to 40% incorporation of starting material.

EXAMPLE 11

Preparation and Analysis of Miconazole Delivery Vehicles

Figure 12:
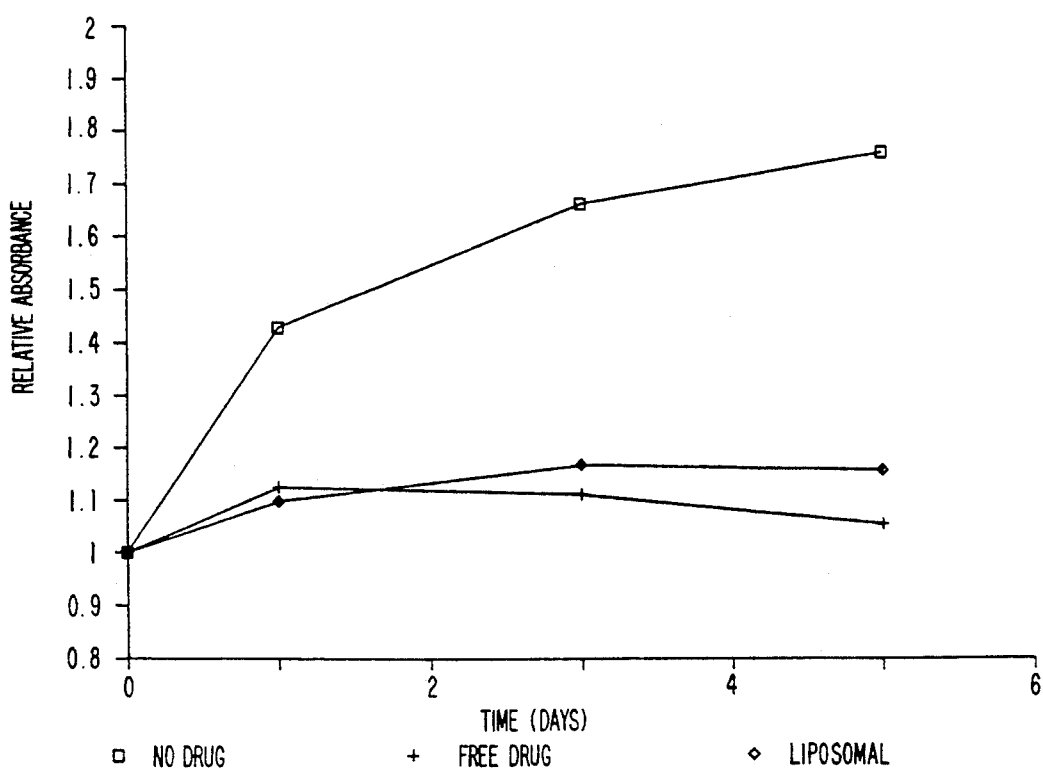
FIG. 12 is a graphical representation showing the time dependence of fungal proliferation in the presence of an active ingredient (miconazole) delivery vehicle of the present invention.

Miconazole (1-[2,4-dichloro-β-[(2,4-dichlorobenzyl)oxy] phenethyl] imidazole nitrate) is an antifungal agent of considerable potency. Its utility, however, is somewhat limited by aqueous solubility and in vivo toxicity and delivery problems. 10 mg miconazole was dispersed in 5 ml 10 mM Tris-HCl buffered 5% dextrose solution by room temperature probe sonication for 5 minutes. 10 mg distearoylphosphatidic acid (DSPA) was added to this suspension and the mixture was sonicated at 65° C. for 15 minutes yielding a white miconazole AAS suspension. This in turn was added to 120 mg of 2:1 DSPC:Chol lipid film, followed by sonication for 15 minutes at 65° C. The resulting liposome-containing solution was centrifuged at 12500 rpm for 15 minutes and successively filtered through 0.45 μm and 0.22 μm filters. The final solution was assayed spectrophotometrically for miconazole by evaporation to dryness under reduced pressure, DMF extraction and subsequent UV absorbance measurement at 273 nm. The assay revealed greater than 95% drug entrapment. The in vitro efficacy of the final solution was tested by growth inhibition of *Candida Albicans* using absorbance at 425 nm to monitor *C. Albicans* concentration in a growth medium. FIG. 12 shows the 425 nm absorbance (relative to initial absorbance) as a function of time for three identical aliquots of *C. Albicans* culture treated with 100 μg/ml free drug, 100 μg/ml liposomal miconazole and no miconazole. This figure clearly demonstrates that free and liposomal miconazole inhibit in vitro growth equally well.

EXAMPLE 12

Preparation of Bisanthrene Delivery Vehicles

Bisanthrene (9,10-anthracenedicarboxaldehyde-bis-[4,5-dihydro-1H-imidazol-2-yl)hydrazone]-dihydrochloride) is a potent chemotherapeutic agent that is soluble in acidic aqueous solution. In the bloodstream, however, the drug is insoluble and precipitates out with toxic consequences. An aqueous solution of the dihydrochloride salt of bisanthrene (20 mg of drug in 5 ml distilled water) was made alkaline by the dropwise addition of concentrated (1M) sodium hydroxide solution, resulting in the precipitation of the insoluble free base. This precipitate was removed by centrifuging and washed with PBS until the pH of the PBS suspension of the drug dropped to approximately 7.4. The total volume of the suspension was adjusted to 5 ml. It was then sonicated with 4 mg of palmitic acid. Sonication was carried out for approximately 5 minutes at 65° C. and resulted in a pale yellow bisanthrene AAS formation (analogous to magnetite AAS formation). The bisanthrene AAS was resuspended in 5 ml PBS and sonicated at 65° C. for 15 minutes at 80 W with 100 mg 2:1 DPSC:CHOL lipid film, yielding a cloudy yellow-white solution. This solution was 0.22 μm-filtered yielding a final liposome-solubilized preparation of bisanthrene, the presence of the drug being evidenced by solution coloration.

EXAMPLE 13

Preparation and Analysis of Cisplatin Delivery Vehicles

Cisplatin (cis-diamminedichloroplatinum (II)) is a well-established chemotherapeutic agent that suffers the disadvantage of major clinical toxicity, particularly nephrotoxicity. 10 mg cisplatin was dissolved/suspended in 2 ml of 5% dextrose solution by probe sonication at 80 W for 2 minutes at 65° C. Some cisplatin dissolved, while the remainder became suspended in the solvent. After addition of about 12 mg dipalmitoyl phosphatidic acid (DPPA), the suspension was resonicated at 65° C. and 80 W for 10 minutes, generating a blue-colored cisplatin-AAS material from an initially yellow solution and suspension. The AAS suspension was diluted to 5 ml with 5% dextrose solution and subsequently sonicated at 25° C. with 100 mg 2:1 DSPC:CHOL. Following centrifugation at 12500 rpm for 5 minutes the product solution was 0.22 μm filtered yielding a solution, similar in appearance to small unilamellar vesicle solutions, which was pale yellow to transmitted light and blue-tinted when viewed by scattered light. Analysis for total platinum in the final solution was carried out by 2:1 complex formation with diethylthiocarbamate and UV absorbance measurement, at 254 nm, of the chloroform extract of this solution. The final platinum concentration in 5 ml solution was determined to be 0.66 mg/ml, corresponding to about 51% drug entrapment. Association of the drug with liposomes was demonstrated by chromatography on a Sephadex G50/80 column, on which the solution migrated as a single band.

We claim:

1. A delivery vehicle for an active ingredient, the delivery vehicle having a size from about 20 nm to about 100 nm in diameter and comprising a lipid material enclosing an amphiphile-associated substrate in the essential absence of a solution-phase inner volume, which includes:

an active ingredient phase, an amphiphilic material capable of associating with the active ingredient and having a polar hydrophilic portion and a lipophilic portion, the polar hydrophilic portion of the amphiphilic material being associated with the active ingredient phase to form the amphiphile-associated substrate; and a single, biocompatible encapsulating monolayer surrounding the amphiphile-associated substrate, comprising molecules having lipophilic tails associated with the lipophilic portion of the amphiphile-associated substrate.

2. The delivery vehicle of claim 1 in which the active ingredient phase comprises a solid, particulate phase.

3. The delivery vehicle of claim 1 or 2 wherein the hydrophilic portion comprises a carboxylic, hydroxyl, amino, phosphato or sulfato group.

4. The delivery vehicle of claim 1 or 2 wherein the lipophilic portion comprises an aliphatic hydrocarbon, cycloaliphatic hydrocarbon, aromatic-substituted aliphatic hydrocarbon, cycloaliphatic-substituted aliphatic hydrocarbon or polyoxyethylene group.

5. The delivery vehicle of claim 4 wherein the amphiphilic material comprises a member selected from the group consisting of fatty acids, phospholipids, diglycerides, triglycerides, alcohols, amines, phosphates and sulfates.

6. The delivery vehicle of claim 5 wherein the lipophilic portion comprises an aliphatic chain of from 10 to 28 carbons in length.

7. The delivery vehicle of claim 1 or 2 wherein the biocompatible encapsulating layer comprises a phospholipid material.

8. The delivery vehicle of claim 7 wherein the amphiphilic material comprises a fatty acid or a phosphatidic acid.

9. A delivery vehicle for magnetite, the delivery vehicle having a size of from about 20 nm to about 100 nm in diameter and comprising a lipid particle enclosing a magnetite amphiphile-associated substrate in the essential absence of a solution-phase inner volume, which includes:

a magnetite active ingredient phase, an amphiphilic material capable of associating with the active ingredient and having a polar hydrophilic portion and a lipophilic portion, the polar hydrophilic portion being associated with the magnetite active ingredient phase to form the magnetite amphiphile-associated substrate, and a single, biocompatible encapsulating monolayer surrounding the magnetite amphiphile-associated substrate, comprising molecules having lipophilic tails associated with the lipophilic portion of the magnetite amphiphile-associated substrate.

10. A process for preparing a delivery vehicle for an active ingredient, the delivery vehicle having a size of from about 20 nm to about 10,000 nm in diameter, the process comprising:

forming an initial aqueous dispersion consisting essentially of an association between a particulate active ingredient which is a solid in the aqueous dispersion and an amphiphilic material consisting of molecules having a polar head group and a hydrophobic tail group, in an aqueous phase to form an amphiphile-associate substrate in the aqueous phase, the polar head groups being associated with the solid, particulate active ingredient, and encapsulating the amphiphile-associated substrate by then adding a material capable of forming a biocompatible encapsulating layer for the substrate, the layer comprising molecules having a lipophilic tail group associated with the hydrophobic tail group of the amphiphile-associated substrate, to form a delivery vehicle enclosing the amphiphile-associate substrate in the essential absence of a solution-phase inner volume.

11. The process of claim 10 wherein the polar head group comprises a carboxylic, hydroxyl, amino, phosphato or sulfato group.

12. The process of claim 10 wherein the hydrophobic tail group comprises an aliphatic hydrocarbon, cycloaliphatic hydrocarbon, aromatic-substituted aliphatic hydrocarbon, cycloaliphatic-substituted aliphatic hydrocarbon, or polyoxyethylene group.

13. The process of claim 12 wherein the amphiphilic material comprises a member selected from the group consisting of fatty acids, phospholipids, diglycerides, triglycerides, alcohols, amines, phosphates and sulfates.

14. The process of claim 13 wherein the hydrophobic tail group comprises an aliphatic chain of from 10 to 28 carbons in length.

15. The process of claim 10 wherein the amphiphilic material comprises a fatty acid or a phosphatidic acid.

16. The process of claim 10 wherein the outer biocompatible encapsulating layer comprises a phospholipid material.

17. A process for preparing a delivery vehicle for an active ingredient, the delivery vehicle having a size of from about 20 nm to about 10,000 nm in diameter, the process comprising:

forming an initial aqueous dispersion consisting essentially of an association between a solid, particulate active ingredient and an amphiphilic material consisting of molecules having a polar head group and a hydrophobic tail group, in an aqueous phase to form an amphiphile-associate substrate in the aqueous phase, the polar head groups being associated with the solid, particulate active ingredient, and encapsulating the amphiphile-associated substrate within a single encapsulating layer, which layer further constitutes an outer biocompatible encapsulating layer, by then adding a material capable of forming a biocompatible encapsulating layer for the substrate, the layer comprising molecules having a lipophilic tail group associated with the hydrophobic tail group of the amphiphile-associated substrate, to form a delivery vehicle enclosing the amphiphile-associate substrate in the essential absence of a solution-phase inner volume.

18. The process of claim 10, 15 or 17 wherein said delivery vehicle has a size of from about 20 nm to about 100 nm in diameter.

19. A process for preparing a delivery vehicle for a magnetite active ingredient, the delivery vehicle having a size of from about 20 nm to about 10,000 nm in diameter, the process comprising:

forming an initial aqueous dispersion consisting essentially of an association between a solid, particulate active ingredient, which active ingredient comprises magnetite, and an amphiphilic material consisting of molecules having a polar head group and a hydrophobic tail group, in an aqueous phase to form a magnetite amphiphile-associated substrate in the aqueous phase, the polar head groups being associated with the solid, particulate magnetite active ingredient, and encapsulating the magnetite amphiphile-associate substrate by then adding a material capable of forming a biocompatible encapsulating layer for the substrate, the layer comprising molecules having a lipophilic tail group associated with the hydrophobic tail group of the magnetite amphiphile-associated substrate, to a form a delivery vehicle enclosing the amphiphile-associated substrate in the essential absence of a solution-phase inner volume.

20. The process of claim 19 including encapsulating the magnetite amphiphile-associated substrate within a single encapsulating layer, which layer further constitutes said outer biocompatible encapsulating layer.

21. The process of claim 19 wherein the amphiphilic material comprises a fatty acid or a phosphatidic acid.

* * * * *